(12) United States Patent
Feldman et al.

(10) Patent No.: US 6,550,480 B2
(45) Date of Patent: Apr. 22, 2003

(54) LUMEN OCCLUDERS MADE FROM THERMODYNAMIC MATERIALS

(75) Inventors: Tatyana Feldman, Newport Beach, CA (US); Wei Wang, Irvine, CA (US)

(73) Assignee: Numed/Tech LLC, Newport Beach, CA (US)

(*) Notice: Subject to any disclaimer, the term of this patent is extended or adjusted under 35 U.S.C. 154(b) by 20 days.

(21) Appl. No.: 09/773,108

(22) Filed: Jan. 31, 2001

(65) Prior Publication Data

US 2002/0129819 A1 Sep. 19, 2002

(51) Int. Cl.⁷ .................................................. A61F 6/06
(52) U.S. Cl. ............................ 128/831; 128/843; 604/1; 604/385.17
(58) Field of Search ........................ 251/11; 128/831, 128/887, 898, 843, 835, 840; 604/1, 385.17

(56) References Cited

U.S. PATENT DOCUMENTS

| | | | |
|---|---|---|---|
| 3,317,629 A | 5/1967 | Quaal | |
| 4,606,336 A | 8/1986 | Zeluff | |
| 4,700,701 A | 10/1987 | Montaldi | |
| 4,788,966 A | 12/1988 | Yoon | |
| 4,959,048 A | * 9/1990 | Seder et al. | 604/8 |
| 5,065,751 A | * 11/1991 | Wolf | 128/831 |
| 5,469,867 A | * 11/1995 | Schimdtt | 128/898 |
| 5,483,027 A | 1/1996 | Krause | |
| 5,488,961 A | 2/1996 | Adams | |
| 5,492,993 A | * 2/1996 | Saam et al. | 528/15 |
| 5,556,396 A | 9/1996 | Cohen et al. | |
| 5,713,078 A | 2/1998 | DeAngelis | |
| 5,814,705 A | 9/1998 | Ward et al. | |
| 5,873,971 A | 2/1999 | Balzar | |
| 5,935,137 A | 8/1999 | Saadat et al. | |
| 5,941,894 A | 8/1999 | Hill | |
| 5,954,715 A | 9/1999 | Harrington et al. | |
| 6,027,470 A | * 2/2000 | Mendius | 604/8 |
| 6,030,416 A | 2/2000 | Huo et al. | |
| 6,056,976 A | * 5/2000 | Markkula et al. | 424/486 |
| 6,082,362 A | * 7/2000 | Webb | 128/846 |
| 6,234,175 B1 | 5/2001 | Zhou et al. | |
| 6,309,384 B1 | * 10/2001 | Harrington et al. | 606/28 |
| 2002/0029013 A1 | * 3/2002 | Paskar | 604/95.01 |

FOREIGN PATENT DOCUMENTS

| | | |
|---|---|---|
| EP | 0 666 279 A2 | 8/1995 |
| JP | 05 200864 A | 8/1993 |

* cited by examiner

*Primary Examiner*—Gene Mancene
*Assistant Examiner*—Frederick C. Nicolas
(74) *Attorney, Agent, or Firm*—Frost Brown Todd LLC

(57) ABSTRACT

Disclosed are occluders and methods of their use. The occluders comprise shape-memory polymeric materials which, when heated above their crystalline melting temperatures, may be deformed from a first configuration into a second configuration. The occluder is then held in the deformed shape until it cools to a temperature below its crystalline melting temperature ($T_m$) whereby it holds the deformed shape of the second configuration by virtue of the recrystallization of the polymeric occluder material. Upon reheating the occluder above its $T_m$, the occluder will resume its original shape. In this manner, an occluder which has been deformed to reduce its diameter may be inserted into and positioned within a target lumen in the body and then allowed to warm to body temperature whereby it resumes its original diameter and results in the occlusion of the lumen. The occluders, according to preferred embodiments, may be used for reversible sterilization of mammals, among other surgical and non-surgical uses.

5 Claims, 2 Drawing Sheets

LUMEN OCCLUDERS MADE FROM THERMODYNAMIC MATERIALS

BACKGROUND OF THE INVENTION

There are many occasions in mammal's life, whether for enhancing quality of life or for medical reasons, where passage of materials through a body lumen needs to be stopped. Such stoppage may be temporary, or it may be permanent or semi-permanent. Generally speaking, the body lumen may include tubes, blood vessels, cavities, canals, or any other lumens where there is an exchange or flow of media or materials, whether in the form of gases, such as air, liquids, such as water or blood or solids, such as cells. For example, an earplug is an occluder for reducing noise. It can also be used for preventing water from entering ears for swimmers. The media in the first case is air, which carries the sound wave, and in the second case is water for swimmers. In another example, an occluder for the fallopian tubes of the female mammal can prevent eggs from moving through the tube, thereby avoiding pregnancy. In a third example, there may be a need for a temporary or permanent closure of blood vessel for certain medical conditions, such as tumor control therapy. An occluder for this application is used to stop the blood flow to a targeted location either for a short period of time or permanently.

In any such occlusion application, an important factor in the proper functioning of the occluder is its size, which should be closely matched with and properly fitted in the targeted lumen of mammals. An undersized occluder will leak, allowing for passage of media which was to be blocked, while an oversized occluder may cause discomfort for the patient or lead to permanent damage to the lumen in which it is placed. Therefore, a practitioner should measure or be aware of the average size of the target lumen of the mammal and then choose an occluder having an appropriate size. Still, mismatch can occur because the targeted lumen in the mammal may not have a regularly defined shape, or the size may be outside the norm. Therefore, preferred designs would employ a material which can adapt and conform to the shape of the individual lumen.

Accordingly, there is a need in providing an occluder device which can adapt and conform to the shape of an individual mammal's lumen. Preferably, the occluder device can be made in a one-size-fits-all design. Optionally, the occluder device can be removed and perhaps reused in appropriate circumstances.

SUMMARY OF THE INVENTION

In accordance with one embodiment of the present invention, there is provided an absorbent occluder. The absorbent occluder comprises a shape memory composition comprising a crystalline domain structure having a crystalline melting temperature ($T_m$) in the range of about 0° to about 37° C. and an absorbent material.

In accordance with another embodiment of the present invention, there is provided a method of occluding a lumen in a living mammal. The method comprises providing an occluder comprising a shape memory composition and an absorbent material, wherein the shape memory portion of the occluder has been deformed to a diameter equal to or smaller than the inner diameter of a target lumen of a living mammal, inserting the occluder into the lumen, and allowing at least the shape memory composition portion of the occluder to warm to the body temperature thereby recovering its shape and generally conforming to the diameter of the target lumen. The shape memory composition portion of the occluder comprises a crystalline domain structure having a crystalline melting temperature ($T_m$) in the range of about 0° to about 37° C.

In accordance with a further embodiment of the present invention, there is provided a method of occluding a lumen in a living mammal. The method comprises providing an occluder deformed to a diameter equal to or smaller than the inner diameter of a target lumen of a living mammal, said occluder comprising a shape memory composition having a glass transition temperature in the range of about −100° to about 20° C. and said composition comprising a crystalline domain structure having a crystalline melting temperature ($T_m$) in the range of about 0° to about 37° C., surgically inserting the occluder into the lumen, and allowing the occluder to warm to the body temperature thereby becoming elastic and conforming to the size and shape of the target lumen. In preferred embodiments, the deformed occluder is provided by a process which includes providing an occluder with a diameter equal to or larger than the inner diameter of the target lumen, warming the occluder to a temperature higher than $T_m$, deforming the occluder until the deformed diameter is smaller than the diameter of the target lumen, and cooling the deformed occluder to a temperature sufficiently lower than $T_m$ to allow the composition to re-crystallize such that the occluder retains the deformed form.

DETAILED DESCRIPTION OF THE PREFERRED EMBODIMENT

In accordance with preferred embodiments of the present invention, body lumens are occluded by use of a shape-memory polymeric occluder sized to fit the target lumen. The occluder is preferably heated above its crystalline melting temperature and deformed from its original configuration, such as by stretching, to a shape having different dimensions as may facilitate placement or implantation into the target lumen. Once the occluder has been deformed as desired, it is held in the deformed shape until it cools to a temperature below its crystalline melting temperature, so that it will retain the deformed shape by virtue of the recrystallization of the polymeric occluder material. Upon reheating the occluder above its crystalline melting temperature, which is preferably above room temperature but below body temperature, the occluder will resume its original shape. In this manner, an occluder which has been deformed to reduce its diameter may be inserted into and positioned within a target lumen and then allowed to warm to body temperature whereby it resumes its original diameter and results in the occlusion of the lumen.

As used herein, the term "lumen" is used to mean a passage or a cavity in a mammal where there is an exchange or flow of gas, liquid, or solid media. Examples of lumens according to this definition include, without limitation, blood vessels, the vas deferens, fallopian tubes, ureters, urethras, vaginas, ear canals, etc. It also includes canals or vessels which have internal flow controls, such as sphincters, capillary beds, etc.

As used herein, the term "occluder" is used to mean a device which is intended to partially or completely block the exchange or the flow of media via the lumen on a temporary or permanent basis.

The "body temperature" of mammals in most cases means 36° to 38° C. However, in some special cases, body temperature could vary beyond this temperature range, depending upon the location in the mammal's body and medical conditions. These cases of various conditions are discussed in the U.S. Pat. No. 5,469,867 and thereby are incorporated fully herein by reference.

In accordance with the present invention, the occlusion of lumens is effected by use of occluders which are comprised largely of at least one polymeric material having "shape memory" properties. In preferred embodiments, the occluder has structural and thermodynamic properties which allow for a reversible transformation of crystalline forming and crystalline melting.

Figure 1:
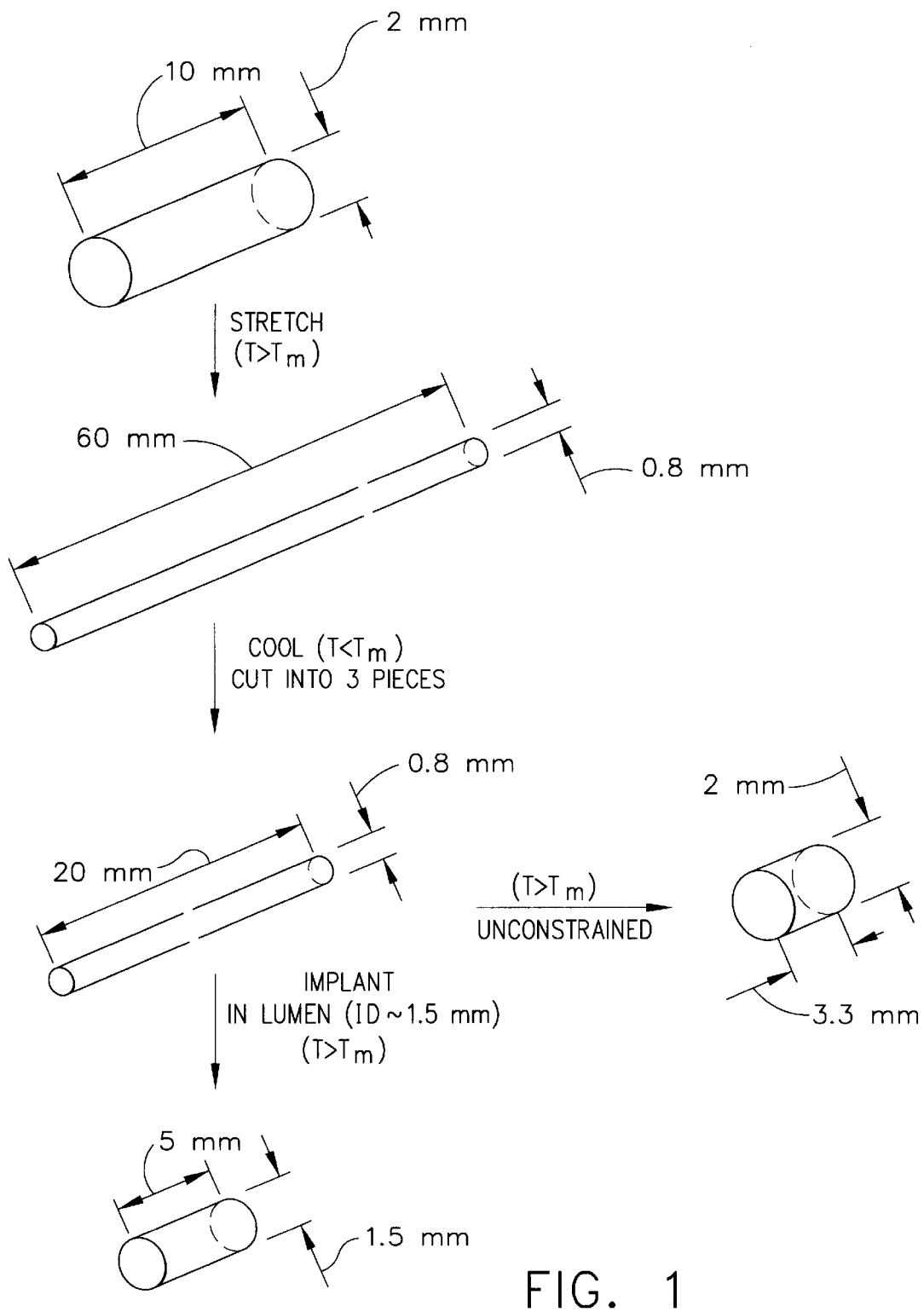
FIG. 1 is a schematic showing the process of melting, deformation, sectioning, recrystallization, and shape recovery of an occluder according to a preferred embodiment of the present invention.

To provide a greater understanding of preferred embodiments of the present invention, the following is given for purposes of illustration, and is not intended to limit the scope of the invention. In this example, it is desired to occlude a target lumen of a mammal having a diameter in the range of 1.0 mm to 1.5 mm. It is also desired that the length of the occlusion in the lumen be no smaller than 5 mm. Using these assumptions, a rod having dimensions measuring about 2 mm in diameter and 10 mm in length is made from a polymeric material having the aforementioned reversible crystalline formation properties. The rod is warmed to a temperature higher than its crystalline melting point, and stretched to a shape that is approximately 60 mm long with a diameter of about 0.8 mm. While stretched, the rod is gradually cooled down to a temperature below its crystal melting point (room temperature for example) thereby allowing re-crystallization to occur. The re-crystallization serves as the force to lock the rod in the stretched form such that when the stretching force is released, the rod remains in the rigid stretched form. This rod is then cut into short pieces, approximately 20 mm in length. The short pieces of rod can be used as size adaptive occluders in mammals for lumens with a diameter in the range of approximately 1–2 mm. When the size adaptive occluder is inserted into lumens in mammals, the body temperature of mammals will melt the crystalline structure of the material. As a result, the rigid rod in the deformed configuration becomes soft and its shape starts to return to its pre-stretched form, i.e. its diameter starts to increase from 0.8 mm up to its pre-stretched 2 mm and its length starts to decrease from 20 mm to about 3.3 mm, assuming full recovery when there is no resistance from surrounding tissue (unconstrained recovery). When the shape recovery occurs inside the lumen of mammals, however, the rod will meet with an increasingly resistant force from the surrounding tissue. When this resistive force equals the recovery force of the material, the shape recovery will stop. If this point is when the interior diameter of the lumen is at approximately 1.5 mm, the short rod will stop shape recovery when its diameter reaches approximately to 1.5 mm. Given the initial properties of this example as discussed above, the length of the recovered rod will be approximately 5 mm or slightly more. In this manner, the size adaptive occluder achieves a snug fit with the lumen of the mammal. The process discussed above is illustrated in FIG. 1 using the exemplary measurements noted herein.

In accordance with preferred embodiments of the present invention, there are provided occluders comprising a polymeric shape memory material. The occluders are of a size and shape which enables them to fit within the lumen of a mammal, preferably fitting snugly against the wall of the lumen. The size and shape of an occluder varies significantly depending on the dimension of the lumen and the intended use of the occluder. For example, an occluder preferably has a diameter of about a fraction of millimeter (e.g. for small blood vessels) to about an inch (e.g. for vaginas). Other sizes are contemplated as may be needed to provide a snug fit within a particular lumen.

In accordance with another preferred embodiment, the occluder further comprises an absorbent material. The absorbent material may be any type known in the art, including, but not limited to, absorbent materials such as cotton and rayon, absorbent structures such as sponges, hydrogel materials such as poly(hydroxyethylmethacrylate) and poly(N-vinylpyrrolidinone), water soluble polymers such as poly (acrylamide), poly(acrylic acid) and its salts, poly (vinylsulfonic acid) and its salts, and polysaccharides. In this embodiment, a portion of absorbent material is surrounded by shape memory material on one or more of its sides or surfaces such that the absorbent material is at least partially exposed to the lumen to allow it to absorb fluids. For embodiments comprising both absorbent materials and the shape memory materials, the occluder preferably has a diameter of about 5 mm to about 40 mm and a length of preferably about 5 mm to about 90 mm. Other sizes are contemplated as may be needed to snugly fit a particular lumen and provide sufficient absorbency.

There are several classes of materials which are suitable for use as the shape-memory material in accordance with preferred embodiments of the present invention. Preferred material compositions have dual thermodynamic properties: i.e. a glass transition temperature ($T_g$) lower than room temperature, preferably in the range of –100° to 20° C.; a crystalline melting temperature ($T_m$) lower than body temperature, preferably in the range of 0° to 37° C. and more preferably in the range of 25° to 35° C. The crystalline or semi-crystalline structure provides the shape memory material with a rigid form at a temperature below $T_m$, and the glass transition property provides the shape memory capability at a temperature above $T_m$. Additional desirable properties of the shape memory material composition include: ability to be stretched about 100% or more of its original length when it is in its elastomer form; ability to solidify and be locked in the stretched form by decreasing the temperature from above $T_m$ to below $T_m$; and the ability to become an elastomer again when the temperature increases to $T_m$ or higher. The examples given below are for illustration purpose only, not to limit the scope of other classes of crystalline materials which may be used for the occluder.

For preferred embodiments in which the occluder is placed inside the body cavity of the mammal, such as in a surgical procedure such as the female sterilization application discussed below, the crystalline melting temperature of the shape-memory occluder material is preferably between about 0° C. and 37° C., more preferably between about 25° C. and about 35° C. Crystalline melting temperatures lower than room temperature (i.e. those below about 20° C.) may be used, but are less preferred because the advantages conferred by the shape-memory characteristics discussed above are not as apparent unless steps are taken to keep the occluder below its $T_m$, such as by cooling it with ice or other cooling material. In other preferred embodiments in which the occluder is placed in a lumen which is accessible from outside the body, such as the vagina or nostril, crystalline melting temperatures on the lower end of the body temperature range are preferred, in that such lumen may not experience full body temperature.

One preferred class of thermodynamic materials are polymers with the main chain crystalline formation structure formed by repeating segments of stereo-regular units. One example is vinyl capped poly[methyl(3,3,3-trifluoropropyl)-siloxane] having a cis/trans ratio of approximately 60/40 or higher as shown below:

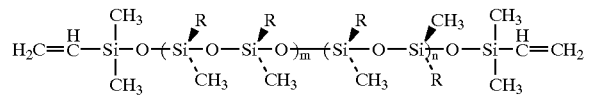

wherein R is CF$_3$—CH$_2$—CH$_2$—

Vinyl Capped Poly[methyl(3,3,3-trifluoropropyl)-siloxane] (Poly-F$_3$)

Poly-F$_3$ can be crosslinked with any of a number of chemicals having multiple Si—H groups, such as tetrakis-(dimethylsiloxyl)silane in the presence of platinum catalyst. The resulting silicone material can be cut into smaller sections (e.g. a sheet can be cut into strips or a rod can be cut into sections) or the material can be cured in molds having the shape and size desired for an individual occluder.

EXAMPLE 1

Preparation of Crosslinked Poly(methyl(3,3,3-trifluoropropyl)-siloxane)

Poly(methyl(3,3,3-trifluoropropyl)-siloxane) with about 60% of cis-stereo structure was prepared in a three-step procedure as follows: In the first step, a difunctional initiator was prepared. Two grams of diphenyl silanediol was dried at 110° C. under vacuum for about 30 minutes in a round bottom flask. After cooling to the room temperature, a mixture of 7.5 ml of dry toluene and 7.5 ml of dry THF were introduced into the flask under the protection of argon. 10 microliters of styrene was also added as a indicator. Butyl lithium (2.5 M in hexane, Aldrich) was added dropwise to the reaction mixture until the solution turned slightly yellow, indicating that a difunctional initiator, lithium diphenyl silanediolate had been formed.

In the second step, 15 grams of cis and trans isomers of 1,3,5-trimethyl-1,3,5-tris(3',3',3'-trifluoropropyl) cyclotrisiloxane (cis- and trans- F$_3$) comprising about 60% cis isomer and about 40% trans isomer were placed in a 100 ml round bottom flask and dried at about 80° C. under vacuum for about 30 minutes. After cooling down to room temperature, 1.5 ml of dry THF and 10 ml of methylene chloride were then added to the flask. About 1.5 ml of the difunctional initiator solution from the first step was added under the protection of argon. The reaction mixture was stirred for about 4 hours at room temperature. To terminate the reaction, about 0.8 ml of vinyldimethylchlorosilane and equivalent amount of triethylamine were added to neutralize the formation of HCl. The reaction mixture was then stirred for about 5 hours to ensure the material was end capped with vinyldimethylsilyl group. After washing with water, the organic layer was dissolved in THF and precipitated from methanol. About 11 grams of poly(methyl(3,3,3-trifluoropropyl)-siloxane) was obtained (73% yield).

In the third step, poly(methyl(3,3,3-trifluoropropyl)-siloxane) was crosslinked with tetrakis(dimethylsiloxy) siloxane. About 10 grams of poly(methyl(3,3,3-trifluoropropyl)siloxane was mixed with 15 microliters of inhibitor (1,3,5,7-tetravinyl-1,3,5,7-tetramethylcyclosiloxane), 70 microliter of tetrakis (dimethylsiloxy)siloxane, and a trace amount of platinum catalyst. The final mixture was degassed and cured in a glass mold at about 130° C. for about 1 hour. The resulting sheet was a clear elastomer with at least 400% elongation at break.

The procedure described above is similar to prior art methods disclosed in U.S. Pat. No. 6,030,416 to Huo et al., Kuo and Saam, *Stereoregularity in Poly[methyl(3,3,3-trifluoropropyl)siloxane]*, Polymer International, 187–195, (1994), and Battjes et al, *Strain-induced crystallization in poly[methyl(3,3,3-trifluoropropyl)siloxane]networks* Macromolecules, vol. 28, 790–792, (1995). Battjes noted that as the cis isomer content increases, the melting temperature also increases. This is shown in Table 1 below, in which the data is taken from the Battjes article:

Table 1. Melting Temperature (T$_m$) vs. Percentage of Cis-F$_3$

TABLE 1

| Melting Temperature (T$_m$) vs. Percentage of Cis-F$_3$ | | | | |
|---|---|---|---|---|
| (Cis-F$_3$) % | 0 | 48 | 62 | 84 |
| T$_m$ (° C.) | N/A | −0.4 | 18.6 | 35.8 |

EXAMPLE 2

A strip of cured silicone made by the process of Example 1 was warmed up to 50° C. and stretched to approximately 400% of its initial length. When it was cooled down in an ice water bath having a temperature of about 1–5° C., the soft stretched silicone strip crystallized in approximately one minute and became rigid. When the stretching force was released, it remained in the rigid stretched form. The same strip was then warmed to body temperature (approximately 37° C.), whereby the crystalline material started to melt. The strip became soft and its shape returned to its pre-stretched form in about one minute.

A second class of thermodynamic materials for use in accordance with preferred embodiments of present invention are polymers with side chain crystalline inducing groups. One preferred member of this class of materials is poly(stearyl methacrylate). The 18 carbon side chain of the material is responsible for the formation of the crystalline structure. For example, monomer of stearyl methacrylate can be polymerized in a mold, such as a glass tube or Teflon plate mold. The finished polymer preferably takes the form of a rod or a sheet, but may be any shape or form desired. The subclass of side chain crystalline materials to which poly (stearyl methacrylate) belongs is characterized by the formula below:

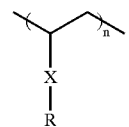

where X may be a carboxyl group or other spacers, such as O, and R is responsible for the formation of crystallinity of the thermodynamic polymer. Examples of preferred R groups include, but are not limited to, alkyl groups having 16 or more carbon atoms. Note that the formula shown above is only part of the polymer backbone structure where a side chain crystalline formation group is attached. The other part of the polymer backbone structure varies depending on the type of the monomer or co-monomers or crosslinkers. As opposed to the main chain crystalline formation polymers discussed above, in this second preferred class of polymers, those with sidechain crystalline inducing groups, the backbone of the polymer is generally not of great importance with respect to the polymer having the desired crystallinity properties. This is because, as the name suggests, the properties are imparted by the side chains such that any of a wide variety of backbone structures, including, but not limited to those comprising substituted or unsubstituted alkyl chains, may be used and still achieve the desired characteristics in the polymer.

EXAMPLE 3

Preparation of Poly(stearyl methacrylate)

In a typical experiment, 10 grams of stearyl methacrylate monomer (Aldrich) was mixed with 20 mg of benzoyl peroxide and stirred until all benzoyl peroxide was dissolved. The reaction mixture was degassed and purged with nitrogen gas three times. The mixture was then transferred into a glass tube or a polypropylene tube having the desired diameter. The tube was sealed to maintain the nitrogen atmosphere and heated to 100° C. for 12 hours followed by heating at 120° C. for 2 hours. The tube was then cooled down to the room temperature. The product was a white solid rod having a observed crystalline melting temperature of about 30° C. The glass transition temperature of pure poly(stearyl methacrylate) is about −100° C.

If necessary, additional crosslinkers, such as ethylene dimethacrylate, can be added to the reaction mixture to increase the elasticity of the resulting polymer. Furthermore, co-monomers, such as methyl methacrylate, can also be added to the reaction mixture to modify the mechanical properties of the resulting copolymers. Still further, other additives can be blended into the composition. Such additives include dye material, wax material, or other components for modifying one or more properties of the polymer.

EXAMPLE 4

A rod of material from Example 3 was warmed to a temperature higher than the melting point of its crystalline structure, at about 35–40° C., wherein the rod became soft and rubbery. It was found that the soft rod could be stretched to about 400% of its unstretched length or more and gradually cooled down to room temperature to become rigid again. In some experiments, the cooling down process was accelerated by immersing the stretched rod in an ice water bath. In the ice water bath, the stretched rod solidifies and freezes in the stretched form in about one minute. When the stretched rod was warmed again to body temperature (about 35° C.), the crystalline form melted to unlock the elasticity of the polymer such that the rod became soft and recovered its pre-stretched shape. As a result, the stretched rod returned to its pre-stretched dimensions.

Other compositions may be used for the present invention include a mixture of a side chain crystalline polymer with a non-crystalline material; a main chain crystalline material with a non-crystalline material; or a combination of them.

The occluder devices and methods of their use according to the present invention have wide applicability in the medical arts. Preferred methods of use include surgical uses in which the occluder device is placed or implanted in a lumen within the body as part of a surgical procedure. Such surgical procedure may be a more conventional procedure performed directly through an percutaneous incision or opening using conventional surgical instruments, or it may be one performed with the use of an endoscope, laparoscope, or other such instrument. In other, non-surgical, embodiments, the occluder device is inserted directly into the lumen without the need for the creation or use of an incision or opening. In such non-surgical embodiments, placement of the occluder may be effected by use of conventional instruments including, but not limited to, forceps, rods, fingers, or a specialized insertion mechanism.

In accordance with preferred embodiments, an occluder device may be removed from the lumen following its placement or implantation therein. The removal of the occluder may occur after a period of a few minutes or hours, such as may occur within the time frame of a single treatment or procedure. In other circumstances, the occluder may be removed after a period of weeks, months, or years following its implantation. Removal of the occluder may be done via a second surgical procedure, whether directly through an incision or opening using surgical instruments, or by means of an instrument such as an endoscope or laparoscope. In the case where the occluder was inserted without the need for surgery or the use of a direct percutaneous opening, such as when it is used in a lumen which opens to the outside of the body, the occluder may be removed through the same opening in which it was inserted. Removal of the occluder in such applications may be done by means of using conventional instruments and devices, including, but not limited to, use of forceps, use of extractors, pulling on a string attached to the occluder, etc.

The occluder devices may be used to occlude a lumen for a time period ranging from a few minutes up to 10 years or more. This range of time may be roughly divided into what one would consider a temporary basis (times ranging up to about a month), a semi-permanent basis (times ranging up to several years), or a permanent basis (about 10 years or more).

In accordance with a preferred method of the present invention, a target lumen in a mammal is chosen, wherein occlusion of such target lumen is desired. An occluder having the desired size to occlude the target lumen is then chosen. The occluder, which is preferably at a temperature below its crystalline melting temperature and in a deformed configuration to aid placement in the lumen, is then placed in the target lumen in the desired location. The occluder is then warmed to a temperature at or above its crystalline melting temperature to allow for it to begin the process of shape recovery, as discussed above. The warning of the occluder may occur simply from exposure to the tissues and fluids within and/or surrounding the lumen, or it may be aided by exposing it to an external source of warmth, such as a lamp or warmed saline.

Once the occluder is in place, it is preferably somewhat soft as it is at or above its $T_m$. As such, it may be removed by any of a number of means, including, but not limited to grasping the occluder and pulling it out of the lumen, grasping the occluder and deforming it to allow it to be dislodged and removed, cutting the occluder into smaller pieces and removing the smaller pieces, and excising the occluder by cutting into the wall of the lumen. Such removal methods may be done using an instrument such as a forceps or trocar, or there may be a built-in removal mechanism such as a removal cord or string which may be grasped by the fingers.

As noted above, preferred methods of use include surgical uses in which the occluder device is placed or implanted in a lumen within the body as part of a surgical procedure. Three preferred surgical uses are discussed below. These preferred methods are merely exemplary, in that surgical applications and methods other than those discussed below are contemplated by the present inventors.

One preferred surgical method is that which allows for the reversible sterilization of female mammals. There are many ways for preventing female mammals from becoming pregnant. Surgical methods include tubal ligation procedures in which the fallopian tubes are cut and the open ends sealed by cauterization or tying ligatures around the tubes. Alternatively, the inner surface of the fallopian tubes may be chemically or thermally burned to create a scar which occludes the tube. Consequently, mammal eggs are blocked from moving through the tube and into the uterus where a fertilized egg could implant and result in pregnancy.

In accordance with the present invention, an occluder sized to have a snug fit within the fallopian tube is inserted into each of the tubes in a surgical procedure. Such occluder would preferably be in the shape of a rod, pellet or disc. Prior to insertion, the occluder is preferably heated, deformed and then cooled in the deformed state, as noted above, such that the diameter during insertion and placement is smaller than its eventual diameter following shape recovery so as to facilitate easy maneuvering and placement of the occluder within the fallopian tube. Once implanted, the occluder may remain in place for an indefinite amount of time, being essentially a permanent form of birth control or sterilization. However, because the occluder is removable as noted above, this form of sterilization would be reversible. Once removed, there should be little if any damage to the fallopian tube, allowing for normal, natural fertilization and conception to occur after removal of the occluder.

In the art, in addition to the surgical methods discussed above, there are examples of mechanical occluder devices, thermosetting silicones, and wax-like materials to block the eggs from moving through the fallopian tubes. However, use of such methods do not offer all of the potential advantages enjoyed by preferred embodiments of the present invention, including being size-adaptive to create a snug fit between the occluder and the surrounding tissue, and, perhaps most importantly, being easily reversible with little if any lasting negative effect from the birth control/temporary sterilization method.

Similarly, reversible sterilization of male mammals may be performed by using occluders in accordance with preferred embodiments of the present invention. Vasectomy is the surgical procedure to cause sterilization of male mammals. In a vasectomy, each vas deferens is surgically interrupted, such as by cutting the tube and then sealing one or both ends such as by cauterization, clips, or sutures. The interruption of this tube effectively blocks the path of sperm cells such that they cannot pass from the testes into the ejaculatory ducts.

In accordance with the present invention, an occluder sized to have a snug fit within the vas deferens is inserted into each of the tubes in a surgical procedure. Such occluder would preferably be in the shape of a rod, pellet or disc. Prior to insertion, the occluder is preferably heated, deformed and then cooled in the deformed state, as noted above, such that the diameter during insertion and placement is smaller than its eventual diameter following shape recovery so as to facilitate easy maneuvering and placement of the occluder into the vas deferens. Once implanted, the occluder may remain in place for an indefinite amount of time, being essentially a permanent form of birth control or sterilization. However, as noted above, this form of sterilization could be reversed by simply removing the occluder in a subsequent procedure. Because less damage is done to the vas deferens in implanting the occluder as compared to a standard vasectomy, it is anticipated that reversal of occlusion-based sterilization will have results far superior to that of vasectomy reversal.

In accordance with another preferred surgical use, occluders may be used to seal off a blood vessel on a temporary or semi-permanent basis. Such method may be used to reduce bleeding or blood loss during surgical procedures in which vessels, especially larger vessels, must be cut or severed, such as heart surgery or transplantation surgery. Such method may also be used to shut off a blood supply to a targeted organ or tissues, such as a tumor. This may be helpful in that it is postulated that cutting off the blood supply to a tumor will reduce or starve off the tumor. Similarly, occluders may be used to isolate the blood supply of a tumor such that high concentrations of chemotherapeutic agents may be placed in the area of the tumor without causing great harm to the surrounding healthy tissues.

The methods involving blood vessel blockage proceed much as discussed above, in that an occluder having an appropriate size and shape in its shape-recovered form to block the target lumen is chosen. The occluder is preferably deformed to allow for ease of placement prior to placement in the lumen. The occluder is then allowed to warm and substantially recover its original, non-deformed, size and shape, thereby occluding the lumen. In some embodiments, the occluder used in these methods may further comprise an absorbent material.

As noted above, the occluders of the present invention also find utility in non-surgical embodiments in which the occluder device is inserted directly into a lumen without the need for the creation or use of an incision or opening, such as for lumens which open directly to the outside of the body of the mammal. Two preferred non-surgical uses are discussed below, both of which are merely exemplary, in that applications and methods other than those discussed below are contemplated by the present inventors. In preferred embodiments, the occluders used in these embodiments further comprise absorbent material such that a portion of absorbent material is surrounded by shape memory material on one or more of its sides or surfaces such that the absorbent material is at least partially exposed to the lumen to allow it to absorb fluids.

Tampons are widely used by females to collect discharge during menstrual periods. Despite the use of excellent absorbent materials, some residual leaking may still occur, particularly after an extended time of wearing. In accordance with the present invention, an occluder comprising an absorbent material and a thermodynamic (shape memory) material is used. The absorbent material is used to absorb blood and other vaginal discharge and the shape memory material is used to provide a snug fit within the vagina and thus prevent leakage. The shape memory material component of the tampon embodiment, as in previously described embodiments, is preferably in a shape deformed configuration at the time of insertion which recovers when warmed to a size and shape sufficient to occlude the lumen.

Figure 2A:
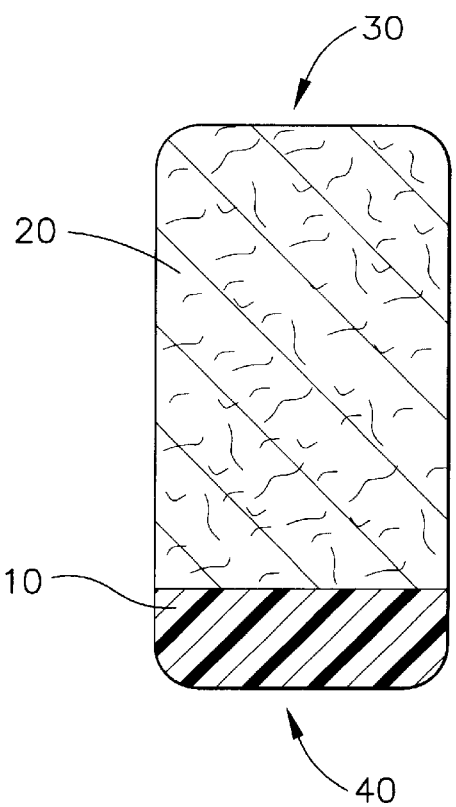
FIGS. 2A and 2B are cross-sectional views of two preferred embodiments of absorbent occluders in accordance with a preferred embodiment.
Figure 2B:
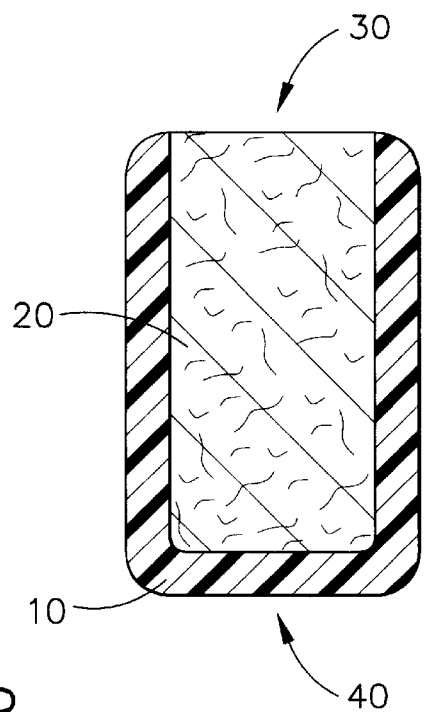

Two exemplary embodiments of absorbent occluder, such as may be used as a tampon, are shown in FIGS. 2A and 2B. In FIG. 2A, the absorbent material 20 is bordered on one side with the thermodynamic material 10. In FIG. 2B, the absorbent material 20 is contained within an open cylinder of thermodynamic material 10. In both cases, the occluder is preferably inserted such that the top end 30 is fully exposed is placed in proximity to the source of fluid to be absorbed.

An occluder of this sort, especially when used as a tampon, may be provided with a string or cord at the bottom end 40 to facilitate removal.

Similarly, smaller sized occluders of the type used in the place of tampons may be used to seal the nostril and absorb blood from nosebleeds. For nosebleed applications, a non-absorbent occluder may also be used.

In accordance with another embodiment of the present invention, the shape memory thermodynamic material may be used as a barrier birth control device. In this embodiment, the material in its initial, undeformed state, would be sized to occlude the upper portion of vagina and/or the cervix and would preferably be deformed so as to have a smaller diameter to facilitate insertion into the vagina and placement at the desired location. Upon completion of the shape recovery process, the occluder would aid in the prevention of conception by providing a physical barrier to the travel of sperm cells in much the same way a diaphragm or cervical cap. Such a barrier birth control occluder device could be a disposable device or it could be reusable. The occluder device could be used with or without additional spermicide, or, the occluder itself could comprise a spermicide. For occluders which comprise spermicide, it may be mixed into the polymer matrix, coated onto the occluder, or otherwise included.

The examples given above are not intended to cover all types of lumen blocking applications in mammals. Rather, they are given to illustrate the principle of utilizing the thermodynamic material for occluding lumens in mammals, whether temporarily or permanently whichever is desirable. In addition, in some applications it may be desirable block a lumen only partially rather than completely seal off the lumen.

What is claimed is:

1. A method of occluding a lumen in a living mammal, said lumen having an inner diameter, comprising:

providing an occluder deformed to a diameter equal to or smaller than the inner diameter of said lumen of a living mammal, said occluder comprising a shape memory composition having a glass transition temperature in the range of about −100° to about 20° C. and said composition comprising a crystalline domain structure having a crystalline melting temperature ($T_m$) in the range of about 0° to about 37° C.;

surgically inserting the occluder into the lumen;

allowing the occluder to warm to the body temperature of said mammal thereby becoming elastic and conforming to the size and shape of the lumen;

wherein said lumen is selected from fallopian tubes, blood vessels, vas deferens, and vagina of said mammal.

2. The method according to claim 1, wherein the shape memory composition comprises cis- and trans-poly[methyl (3,3,3-trifluoropropyl)]siloxane with cis- content of about 40% or higher.

3. The method according to claim 1, wherein the shape memory composition comprises poly(stearyl methacrylate).

4. The method of claim 1 wherein the lumen is a fallopian tube.

5. The method according to claim 1, wherein the deformed occluder is formed by a process comprising:

providing an occluder with a diameter equal to or larger than the inner diameter of the lumen;

warming the occluder to a temperature higher than $T_m$, such that it becomes elastic;

deforming the occluder until the deformed diameter is smaller than the diameter of the lumen;

cooling the deformed occluder to a temperature sufficiently lower than $T_m$ to allow the composition to re-crystallize such that the occluder retains the deformed form.

* * * * *